(12) United States Patent
Liu et al.

(10) Patent No.: US 7,202,947 B2
(45) Date of Patent: Apr. 10, 2007

(54) DEPTH-RESOLVED FLUORESCENCE INSTRUMENT WITH ANGLED EXCITATION

(75) Inventors: Quan Liu, Madison, WI (US); Nirmala Ramanujam, Madison, WI (US); Changfang Zhu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 18 days.

(21) Appl. No.: 10/986,605

(22) Filed: Nov. 12, 2004

(65) Prior Publication Data

US 2005/0143663 A1 Jun. 30, 2005

Related U.S. Application Data

(63) Continuation-in-part of application No. 10/322,907, filed on Dec. 18, 2002, now Pat. No. 6,825,928.

(60) Provisional application No. 60/341,971, filed on Dec. 19, 2001, provisional application No. 60/370,134, filed on Apr. 5, 2002.

(51) Int. Cl.
*G01N 21/64* (2006.01)
*A61B 5/00* (2006.01)

(52) U.S. Cl. ............... 356/317; 250/458.1; 600/317

(58) Field of Classification Search ............... 356/317, 356/318, 417; 250/458.1–461.1; 600/317
See application file for complete search history.

(56) References Cited

U.S. PATENT DOCUMENTS

| | | | |
|---|---|---|---|
| 6,014,204 A | 1/2000 | Prahl et al. | |
| 6,423,956 B1* | 7/2002 | Mandella et al. | 250/201.3 |
| 2002/0080357 A1* | 6/2002 | Dana | 356/445 |
| 2005/0148834 A1* | 7/2005 | Hull et al. | 600/317 |

* cited by examiner

*Primary Examiner*—F. L. Evans
(74) *Attorney, Agent, or Firm*—Quarles & Brady, LLP (57) ABSTRACT

A fluorescence instrument illuminates the surface of tissue with light of a selected wavelength and light emanating from the tissue due to fluorescence is collected. The angle of illumination of tissue surface and/or collection of fluorescence is changed to probe at various depths beneath the surface of the tissue for a fluorescence layer. Three embodiments of the instrument are described.

17 Claims, 11 Drawing Sheets

DEPTH-RESOLVED FLUORESCENCE INSTRUMENT WITH ANGLED EXCITATION

CROSS-REFERENCE TO RELATED APPLICATIONS

This application is a continuation-in-part of U.S. patent application Ser. No. 10/322,907, filed on Dec. 18, 2002 now U.S. Pat. No. 6,825,928 and entitled "Depth-Resolved Fluorescence Instrument" which claims the benefit of U.S. Provisional Application No. 60/341,971, filed on Dec. 19, 2001 and entitled "Quantitative Fluorescence Imaging", and U.S. Provisional Application No. 60/370,134, filed on Apr. 5, 2002 and entitled "Novel Probe Design For Measuring Depth Dependent Fluorescence From Epithelial Tissues".

STATEMENT REGARDING FEDERALLY SPONSORED RESEARCH

This invention was made with government support under Grant No. CA082710 awarded by the National Institute of Health. The United States Government has certain rights in this invention.

BACKGROUND OF THE INVENTION

The field of the invention is fluorescence spectroscopy and imaging, and in particular, the use of fluorescence to detect epithelial pre-cancers and cancers.

Fluorescence spectroscopy and imaging in the ultraviolet-visible (UV-VIS) wavelength spectrum is an exciting new modality for detecting human epithelial pre-cancer and cancer. Fluorescence spectroscopy is performed by irradiating the tissue surface with light and detecting the fluorescent light emitted by "fluorophores" in the tissue. The fluorophores may be "endogenous" molecules that absorb the impinging photons and emit photons at a different wavelength, or they may be "exogenous" fluorophores such as injected photosensitizing agents. This emerging technology has shown promising results for detecting early neoplastic growth in a variety of organ sites including the colon, bronchus, cervix, oral cavity, skin and bladder. Noninvasive and fast detection of epithelial pre-cancers and early cancers through the use of fluorescence spectroscopy can significantly improve the efficacy and reduce cost of cancer screening and diagnostic programs.

One of the most widely explored applications of fluorescence spectroscopy is the detection of endoscopically invisible, early neoplastic growth in epithelial tissue sites. Early neoplastic growth refers to pre-malignant changes such as dysplasia and carcinoma in situ (CIS), which precede malignancy, i.e., invasive carcinoma. Currently, there are no effective and commonly accepted diagnostic techniques for these early tissue transformations. Fluorescence spectroscopy is ideally suited for this application because of its ability to examine tissue surfaces, rather than tissue volumes, and the ability to deploy this technology in an endoscopic device. If fluorescence spectroscopy can be applied successfully as a diagnostic technique in this clinical context, it may increase the potential for curative treatment, and thus, reduce complications. In addition to the potential for improved patient outcome, the fast and noninvasive nature of this diagnostic technique may also reduce health care costs.

Figure 1:
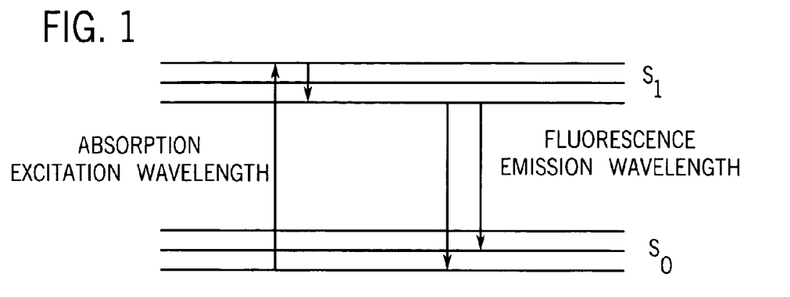
FIG. 1 is an energy level diagram illustrating the phenomena of absorption and fluorescence.
Figure 2A:
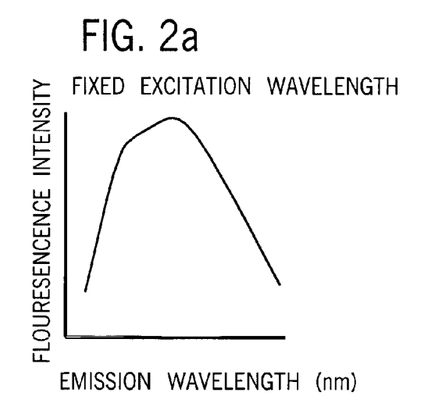
FIGS. 2a–2d are graphic representations of different fluorescence characteristics.
Figure 2B:
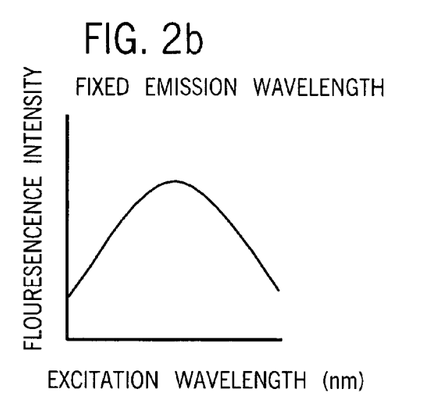
Figure 2C:
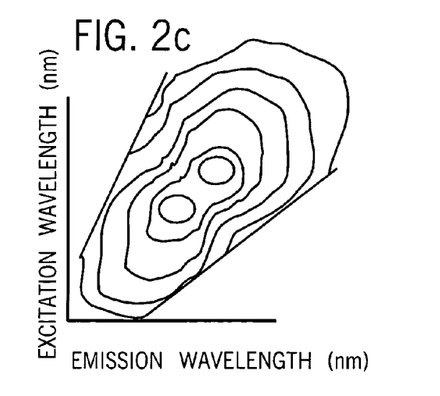
Figure 2D:
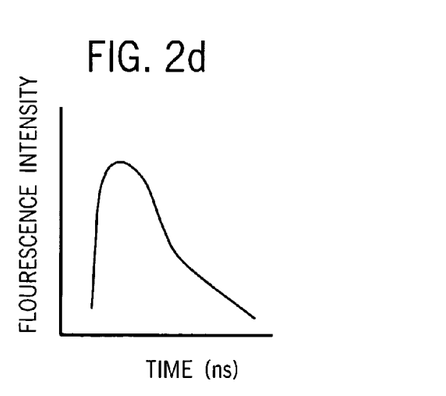

Referring to FIG. 1, when a biologic molecule is illuminated at an excitation wavelength, which lies within the absorption spectrum of that molecule, it will absorb photons' energy and be activated from its ground state (state of lowest energy; $S_0$) to an excited state (state of higher energy; $S_1$). The molecule can then relax back from the excited state to the ground state by generating energy in the form of fluorescence, at emission wavelengths, which are longer than the excitation wavelength. The phenomenon of fluorescence displays several general characteristics for a particular biologic molecule. First, due to losses in energy between absorption and emission, fluorescence occurs at emission wavelengths, which are always red-shifted, relative to the excitation wavelength. Second, the emission wavelengths of fluorescence are independent of the excitation wavelength. Third, the fluorescence spectrum of a biologic molecule is generally a mirror image of its absorption spectrum. The fluorescence of a biologic molecule is characterized by its quantum yield and its lifetime. The quantum yield is simply the ratio of the energy converted to fluorescence to the energy absorbed. The lifetime is defined as the average time the biologic molecule spends in the excited state before returning to the ground state. The fluorescence quantum yield and lifetime are modified by a number of factors that can increase or decrease the energy losses. For example, a molecule may be non-fluorescent as a result of a large rate of non-radiative decay (thermal generation).

Fluorescence spectroscopy is the measurement and analysis of various features that are related to the fluorescence quantum yield and/or lifetime of a biologic molecule (s). The fluorescence intensity of a biologic molecule is a function of its concentration, its extinction coefficient (absorbing power) at the excitation wavelength, and its quantum yield at the emission wavelength. A fluorescence emission spectrum represents the fluorescence intensity measured over a range of emission wavelengths, at a fixed excitation wavelength. Conversely, a fluorescence excitation spectrum is a plot of the fluorescence intensity at a particular emission wavelength, for a range of excitation wavelengths. A fluorescence, excitation-emission matrix (EEM) is a two dimensional contour plot, which displays the fluorescence intensities as a function of a range of excitation and emission wavelengths. Each contour represents points of equal fluorescence intensity. Finally, fluorescence lifetime measurements are represented as the fluorescence intensity distributed over a very short time scale, at a fixed excitation-emission wavelength pair. FIGS. 2a–2d are graphic illustrations of a fluorescence (a) emission spectrum, (b) excitation spectrum, (c) EEM and (d) decay profile.

Table 1 shows a list of biologic endogenous fluorophores and their excitation and emission maxima. These endogenous fluorophores include the amino acids, structural proteins, enzymes and coenzymes, vitamins, lipids and porphyrins. Their excitation maxima range lies between 250 and 450 nm (which spans the ultraviolet and visible spectral range), whereas their emission maxima range lies between 280 and 700 nm (which spans the ultraviolet, visible and near-infrared spectral range). Fluorophores that are believed to play a role in transformations that occur in the neoplastic process in tissue, are the amino acids, tryptophan, the structural protein, collagen, the co-enzymes, NADH and FAD and porphyrins.

TABLE 1

| Endogenous Fluorophores | Excitation Maxima (nm) | Emission Maxima (nm) |
|---|---|---|
| Amino acids | | |
| Tryptophan | 280 | 350 |
| Tyrosine | 275 | 300 |
| Phenylalanine | 260 | 280 |
| Structural Proteins | | |
| Collagen | 325, 360 | 400, 405 |
| Elastin | 290, 325 | 340, 400 |
| Enzymes and Coenzymes | | |
| FAD, Flavins | 450 | 535 |
| NADH | 290, 351 | 440, 460 |
| NADPH | 336 | 464 |
| [NADH, reduced nicotinamide dinucelotide; NAD(P)H, reduced nicotinamide dinucleotide phosphate; FAD, flavin adenine dinucleotide.] | | |
| Vitamins | | |
| Vitamins A | 327 | 510 |
| Vitamins K | 335 | 480 |
| Vitamins D | 390 | 480 |
| Vitamins $B_6$ compounds | | |
| Pyridoxine | 332, 340 | 400 |
| Pyridoxamine | 335 | 400 |
| Pyridoxal | 330 | 385 |
| Pyridoxic acid | 315 | 425 |
| Pyridoxal phosphate | 5'–330 | 400 |
| Vitamin $B_{12}$ | 275 | 305 |
| Lipids | | |
| Phospholipids | 436 | 540, 560 |
| Lipofuscin | 340–395 | 540, 430–460 |
| Ceroid | 340–395 | 430–460, 540 |
| Porphyrins | 400–450 | 630, 690 |

Fluorescence spectroscopy of turbid media such as tissue depends on any of a number of factors. It depends on the concentration and distribution of fluorophore(s) present in the tissue, as well as the biochemical/biophysical environment, which may alter the quantum yield and lifetime of the fluorophore(s). For example, epithelial tissues, generally have two primary sub-layers: a surface epithelium and an underlying stroma or submucosa; the specific fluorophores, as well as their concentration and distribution can vary significantly in these two tissue layers with a neoplastic change. Fluorescence spectroscopy of turbid media such as tissue also depends on the absorption and scattering that results from the concentration and distribution of nonfluorescent absorbers and scatterers, respectively, within the different sub-layers of the tissue.

The effect of the aforementioned factors on fluorescence spectroscopy of tissue is wavelength-dependent. First, the fluorophores that have absorption bands that lie in the same wavelength range as the excitation light will be excited and hence, emit fluorescence. The absorption and scattering properties of the tissue will affect light at both excitation and emission wavelengths. Therefore, only those fluorophores contained in the tissue layers to which the excitation light penetrates and from which, the emitted light can escape the tissue surface will produce measurable fluorescence. Elastic scattering events in tissue are caused by random spatial variations in the density, refractive index, and dielectric constants of extracellular, cellular and subcellular components. Tissue scattering generally decreases monotonically with increasing wavelength over the ultraviolet (UV), visible (VIS) and near-infrared (NIR) spectral regions.

Although absorption in tissue is strongly wavelength-dependent, it tends to generally decrease with increasing wavelengths. Consequently, the penetration depth of light, which is primarily a function of the tissue absorption properties, decreases from several centimeters to a few hundred microns, from the near infrared to the ultraviolet. For example, in the UV spectral region, the penetration depth of light in tissue is approximately 225 μm at 337 nm.

The illumination and collection geometry of the excitation and the emitted light, respectively, can also affect the fluorescence measurement from tissue, with respect to both the intensity and line shape. This may be attributed to the fact that although the fluorescence is generated approximately isotropically from the fluorophores within a medium, the fluorescence emitted from its surface may range from isotropic to anisotropic depending on whether the medium is highly absorbing, dilute or turbid. Monte Carlo simulations have been used extensively to simulate light distribution in turbid media to explore the effect of absorption and scattering on the fluorescence emitted from the surface, using finite excitation beam profiles and complex excitation and emission geometries.

Figure 3:
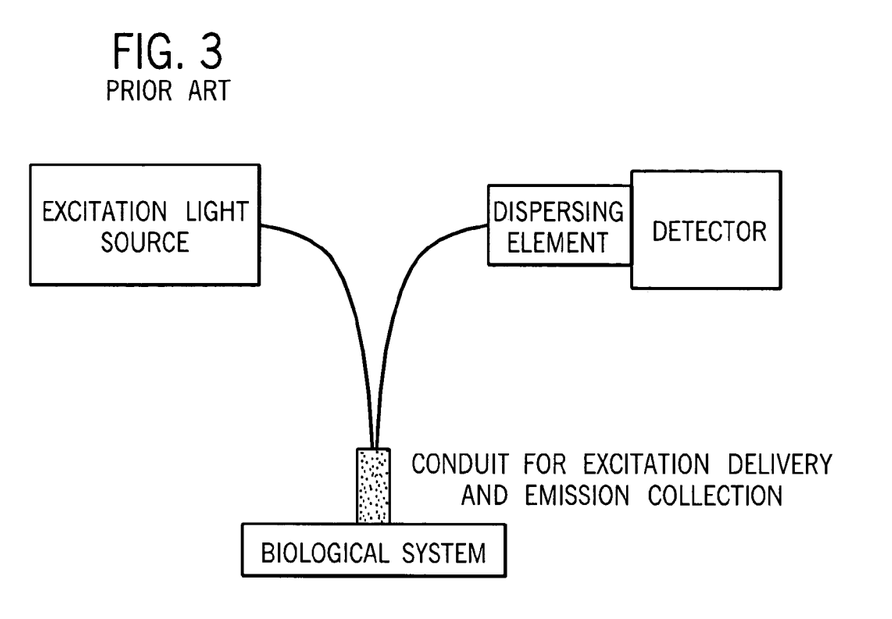
FIG. 3 is a block diagram of a conventional fluorescence spectroscopy instrument.

Fluorescence measurements have been performed on biologic fluids, single cells, cell suspensions, frozen tissue sections and from bulk tissues, both in vitro and in vivo. The various types of instruments employed for these measurements, essentially have the same basic components. A schematic of the basic components of such an, instrument is shown in FIG. 3. It consists of a monochromatic excitation light source, a flexible, delivery and collection conduit for the delivery of excitation light to and the collection of the emitted light from the biologic medium, a dispersing element, which separates the emitted light into its respective wavelengths and a detector, which measures the intensity at the emission wavelength (s).

Generally, monochromatic excitation light sources are used and include ultraviolet and visible arc lamps (mercury, xenon) followed by a bandpass filter and continuous wave (Argon ion-ultra-violet lines, Helium—Cadmium-442 nm) or pulsed lasers (nitrogen-337 nm; the addition of dyes in an attached resonant cavity provides additional visible wavelengths). Lasers have the advantage of efficient coupling into fiber-optic probes. However, filtered arc lamps have the advantage of excitation wavelength tunability, when used with a series of band pass filters or a monochromator and they are generally, more portable. It should be noted that pulsed lasers, with very short pulse durations (in the order of nanoseconds) are necessary when the biologic medium needs to be illuminated with pulsed excitation light for gated detection (which provides effective rejection of ambient light during florescence measurements) and for fluorescence lifetime measurements.

Two approaches are used to illuminate and collect light from tissues. The first approach is to use fiber-optic probes that are placed directly in contact with the tissue (contact approach), and the second approach is to use a series of lenses to project the light onto the surface and collect it, in a similar manner (non-contact approach). With the contact approach, variable pressure on the biologic medium may distort the fluorescence spectrum. However, with the non-contact approach, the fluorescence intensity will vary with the variable, source-sample and sample-detector distance. In general, the contact approach is used for steady-state and time-resolved, fluorescence measurements from small tissue areas, whereas the non-contact approach is more suited for fluorescence imaging from relatively larger areas of tissue.

Light can be spectrally dispersed using a monochromator or a spectrograph, which are both dispersing components. A monochromator presents one wavelength or band pass at a time of the input light from its exit slit, whereas a spectrograph presents a range of wavelengths of the input light, simultaneously at the exit focal plane. Monochromators can be used as filters in conjunction with arc lamps to produce monochromatic excitation light at a series of wavelengths (if only several excitation wavelengths are needed, band pass filters are more appropriate). Monochromators can also be used to disperse the emitted light into its respective wavelengths, each of which can be detected serially using a single-channel detector. However, spectrographs can be used to disperse the emitted light into its respective wavelengths, simultaneously, for multi-channel detection.

The important considerations in choosing a detector are the type of measurements being made, i.e., single wavelength versus multi-wavelength and single-pixel (small area measurements) versus multi-pixel (large area measurements). Fluorescence measurements from single-pixels can be made either using a single-channel or multi-channel detector. If fluorescence intensity at only one or several wavelengths is being measured, single-channel, photo emissive tubes called photo multiplier tubes (PMT) or semiconductor based, avalanche photodiodes (APD), with band pass filters can be used. For fluorescence spectroscopy, a spectrograph coupled to a multi-channel, photo diode array is appropriate. Fluorescence spectroscopy can also be performed using a monochromator coupled to a PMT. In the case of fluorescence imaging from multiple pixels, a two-dimensional, charged coupled device (CCD) camera, with band pass filters may be employed. To reduce or eliminate the detection of ambient light, a detector with an intensifier for fast gating (several nanoseconds) is used in conjunction with a pulsed excitation light source. Also, in order to minimize the detection of the back-scattered excitation light, which is much stronger than the weaker emitted light, optical components, such as long pass or dichroic filters may be employed in front of the detection system.

Single-pixel (<2 mm, diameter of tissue area) measurements of tissue fluorescence spectra, in vivo have been performed mostly using a pulsed excitation light source, a fiber-optic probe (contact approach), a spectrograph and an intensified photo diode array. The transient fluorescence decay profiles at a specific excitation-emission wavelength pair have also been measured using a similar instrument, except that the spectrograph and multi-channel, photo diode array have been replaced by a filtered, single-channel PMT or APD. Finally, fluorescence imaging from multiple pixels of tissue, in vivo (tissue area is a few centimeters in diameter) has been performed with a non-contact approach using a continuous wave laser in combination with a band pass filter and a CCD camera. Measurements with single-pixel and multi-pixel instruments generally require several seconds to a minute in a clinical setting.

Fluorescence spectroscopy in the ultraviolet and visible spectral regions has been developed and employed to differentiate diseased from non-diseased tissues, in vivo. The altered biochemical and morphologic state that occurs as tissue progresses from a non-diseased to diseased state, is reflected in the spectral characteristics of the measured fluorescence. This spectral information can be compared to tissue histology, the current gold standard, which indicates the absence or presence and grade of disease. Mathematical algorithms can then be developed and used to classify tissues into their respective histologic category, based on their spectral features. These mathematical algorithms can be implemented in software, thereby enabling fast, non-invasive, automated screening and diagnosis in a clinical setting.

There are generally two steps involved in the development of a mathematical algorithm, which is based on fluorescence spectroscopy. The first step is to dimensionally reduce the measured spectral variables. The second step is to develop a classification scheme for the discrimination of these useful spectral parameters into relevant histologic/histopathological categories. The development of current mathematical algorithms based on fluorescence spectroscopy can be classified broadly into three categories: 1) algorithms based on qualitatively selected spectral variables (fluorescence intensities at several emission wavelengths), 2) algorithms based on statistically selected spectral parameters (a more robust evaluation and use of all the measured spectral information) and 3) algorithms based on parameters that reflect the biochemical and/or morphologic features of the tissue. Classification schemes employ either a binary or probability based discrimination. In most cases, algorithms are based on qualitatively or statistically selected spectral variables in conjunction with binary classification methods.

While current fluorescence spectroscopy and imaging methods detect neoplastic tissue areas, their sensitivity to the neoplastic layer in tissue is limited by how much of the probing volume intercepts the target of interest. In other words, the probing depth is fixed by the illumination and collection geometry. However, the depth and thickness of the neoplastic growth can vary and the sensing volume may not be optimized for maximal contrast. Being able to maximize the contrast between the neoplastic growth and normal tissue will significantly enhance the diagnostic capability of this technology.

SUMMARY OF THE INVENTION

The present invention employs a fluorescence instrument and method to characterize the depth dependent distribution of a fluorescent target (e.g., pre-cancer or cancer) in a turbid medium (e.g., epithelial tissue). More specifically, a fluorescence strategy is employed in which each discrete site is examined with illumination that is incident at different angles or is collected at different angles to measure the depth dependent distribution of the fluorescence target.

A general object of the invention is to maximize the fluorescence contrast from pre-cancerous and early cancerous growth in human epithelial tissues through the detection of endogenous fluorophores and contrast agents at various depths. This is achieved by tilting the illumination probe or the detection probe at an angle $\theta$ relative to the axis perpendicular to the tissue surface. Changing the angle $\theta$ enables the detection of fluorescence from a wide range of tissue depths in epithelial tissue.

Another object is to provide a fluorescence instrument which enables the measurement of fluorescent targets at various depths below the surface of a turbid medium such as tissue. This depth-profiling fluorescence instrument is adaptable to current endoscopic optical imaging systems without significantly increasing their complexity or cost.

The foregoing and other objects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

GENERAL DESCRIPTION OF THE INVENTION

The feasibility of probing the depth and thickness of a fluorescent target in a turbid medium via fluorescence detection using variable angle, illumination or detection on the sample surface will now be described. First, a theoretical model of a biologically relevant system is established. Next, a Monte Carlo code was developed to simulate fluorescent light propagation through this medium. Then, simulations were performed for a range of coincident, illumination-collection aperture-angles on the surface of the medium.

Figure 4:
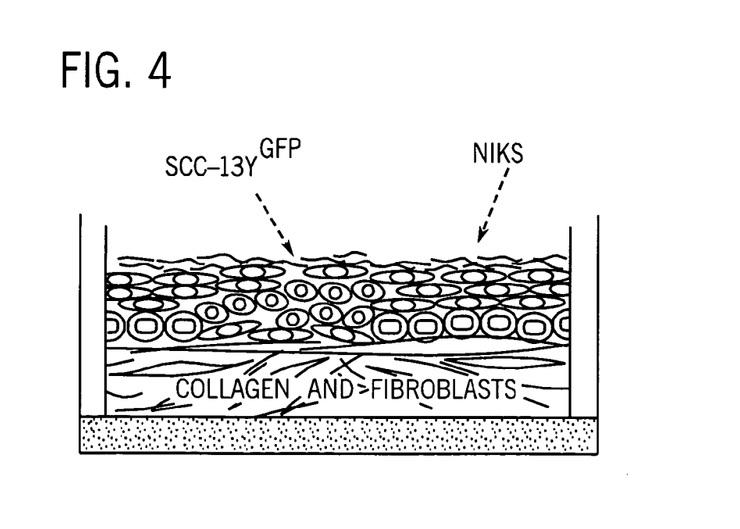
FIG. 4 is an illustration of a tissue culture model of squamous cell carcinoma.

The biological model: A tissue culture model of squamous cell carcinoma (SCC) is shown in FIG. 4. The tissue culture has two layers; a superficial epithelium that is several cell layers thick and which, consists of normal immortalized keratinocytes (NIKs), and an underlying extracellular matrix, which consists of collagen and fibroblasts. The SCCs are inserted into the basal membrane of the epithelium and these cells proliferate over time. It has been shown that the SCC proliferation progresses upward within the epithelium before these cells progress downward and invade the basement membrane. The SCCs can be transfected with the molecular reporter, green fluorescent protein (GFP). Although the SCC tissue culture model has no vasculature, its structure and biological properties mimic that of intact epithelial neoplasia very well.

Figure 5:
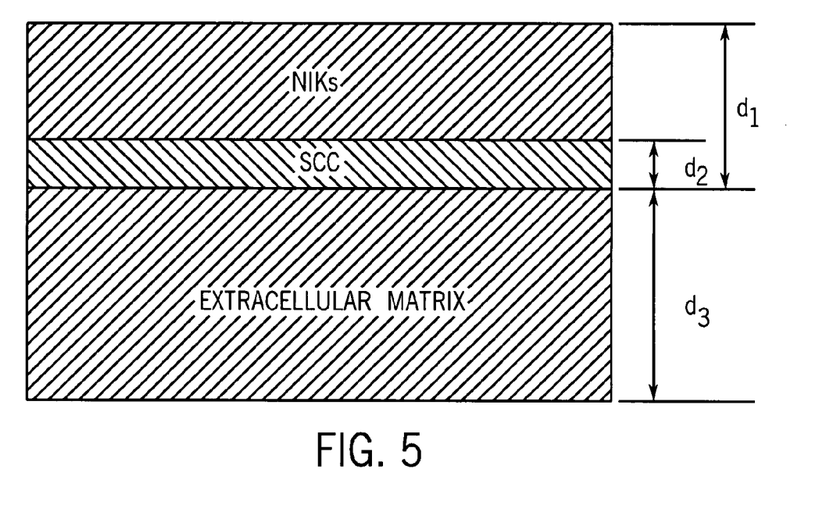
FIG. 5 is a schematic representation of a tissue culture model.

The theoretical model: A theoretical model that closely approximates the tissue culture system is shown in FIG. 5. The model has two primary layers; a normal epithelium layer, which consists of NIKs and an underlying extracellular matrix layer. To simulate the proliferation of SCCs, an additional layer is introduced in the base of the epithelium, the thickness of which ranges from zero to the full thickness of the epithelium, to signify the extent of proliferation. The following parameters are identified for the theoretical model: (1) the dimensions and (2) the optical properties and fluorescence efficiency of each layer, at a particular excitation and emission wavelength. High-resolution fluorescence imaging was used to characterize the auto fluorescence distributions in cross-sections of freeze-trapped neoplastic and non-neoplastic human cervical tissues at the excitation-emission wavelength pairs: 365, 460 nm and 460, 520 nm. The results of this study were used to define the parameters of the theoretical model.

Table 2 summarizes the parameters of the model. The thickness of the NIKs and extracellular matrix layer was defined from the results of cervical tissue studies. The thickness of the SCC layer was assumed to be, variable with maximal thickness equivalent to that of the epithelium, while the total thickness of the epithelium layer and SCC layer were fixed. Therefore, both the depth and the thickness of the SCC layer were varied simultaneously. The lateral dimension of the model is assumed to be, infinitely wide. The auto fluorescence properties of the cervical tissues at the excitation emission wavelength pair, 460, 520 nm were used to assign the fluorescence efficiency values of the NIKs, SCC and extracellular matrix layers. Fluorescence characterization of GFP tagged SCCs (abbr. SCC-GFP) in suspension was performed. The SCC-GFP fluorescence efficiency was maximal near the excitation-emission wavelength pair, 460, 520 nm and was a factor of fourteen higher than the auto fluorescence of SCCs in suspension. The absorption coefficient ($\mu_a$), reduced scattering coefficient ($\mu_s'$) and the anisotropy factor (g) at 460 and 520 nm were obtained from the literature. As a first approximation, these values were assumed to be, identical for all three layers of the model. The refractive index of the model was set at 1.37.

TABLE 2

Parameters of the model (NIKs-normal immortalized keratinocytes, SCC-squamous cell carcinoma, SCCGFP-green fluorescent protein (GFP) transfected SCCs, $\mu_a$-absorption coefficient, $\mu_s'$-reduced scattering coefficient, g-anisotropy, $\lambda_{exc}$-excitation wavelength and $\lambda_{emm}$-emission wavelength).

| Layer | Thickness (μm) | Fluorescence Efficiency at $\lambda_{exc}$, $\lambda_{emm}$: 460, 520 nm | $\mu_a$, $\mu_s'$, (1/cm) and g at $\lambda_{exc}$: 460 nm | $\mu_a$, $\mu_s'$, (1/cm) and g at $\lambda_{emm}$: 520 nm |
|---|---|---|---|---|
| NIKs | 450 | 0.2 | 12, 7.2, 0.94 | 8.3, 7.52, 0.94 |
| SCC | 0–450 | 0.05 | 12, 7.2, 0.94 | 8.3, 7.52, 0.94 |
| SCCGFP | | 0.7 | | |
| Extracellular Matrix | 2000 | 0.6 | 12, 7.2, 0.94 | 8.3, 7.52, 0.94 |

Computational modeling of fluorescent light propagation in the model was carried out using software that was modified from a three-dimensional, weighted-photon Monte Carlo code. The Monte Carlo method simulates the random walk of "discrete photons'" in a turbid medium that contains absorbers and scatterers. The two key decisions are: (1) the mean free path for a scattering and absorption event, and (2) the direction in which the photon moves after a scattering event. At a boundary, the photon is either reflected or moves across the interface. The number of photons required depends on the precision needed.

A two-layered epithelial tissue model with dimensions of the normal human cervix was established for fluorescence simulations with the novel, angled illumination probe. The human cervix was chosen as the theoretical tissue model for this study because the fluorescence efficiencies and epithelial thickness have been quantitatively characterized in previous studies. The thickness of the epithelial layer and that of the stromal layer were fixed at 450 and 2,050 μm, respectively. A thickness of 450 μm was chosen for the epithelial layer to approximate the average thickness of the normal cervical epithelium. The thickness of the stromal layer was set at 2,050 μm to represent an infinitely thick tissue. The axial and radial grid sizes were set at 10 and 100 μm, respectively, and the number of axial and radial grids were set at 250 and 50, respectively to define the region of interest within the epithelial tissue model. Optical properties corresponding to an excitation-emission wavelength pair of 460–520 nm were designated for the theoretical tissue model (Table 3).

TABLE 3

Optical Properties Used For The Monte Carlo Modeling Of Fluorescent Light Transport In An Epithelial Tissue Model

| Optical Property Set | Fluorescence Efficiency | Layers | $\mu_a, \mu_s$ (1/cm) at $\lambda_{exc}$ | $\mu_a, \mu_s$ (1/cm) at $\lambda_{emm}$ |
|---|---|---|---|---|
| (460, 520 nm) | 0.2 | Epithelium | 2.4, 94.0 | 1.8, 80.0 |
| | 0.6 | Stroma | 5.0, 255.0 | 5.0, 220.0 |

The optical property set was used in the fluorescence simulations in order to compare the fluorescence detected with the angled illumination probe to previous approaches for depth-resolved fluorescence detection from epithelial tissues. The fluorescence efficiencies of the epithelial and stromal layers at 460–520 nm were defined from the results of previous human cervical tissue studies. The anisotropy factor (g) and index of refraction (n) of the epithelial tissue model were set to 0.94 and 1.37, respectively.

For fluorescence simulations with the angled probe, the fiber-optic probe geometry on the tissue surface consisted of a single illumination fiber and a single collection fiber, each with a diameter of 200 μm and a of 0.22. In these simulations, the illumination fiber tilt angle was set to 0°, 15°, 30° and 45° relative to the axis perpendicular to the tissue surface while the collection fiber was kept perpendicular to the tissue surface. At each illumination fiber tilt angle, the center-to-center distance between the illumination and collection fiber was varied from 200 μm to 1,000 μm in 200 μm increments. Additionally, at an illumination fiber tilt angle of 45-degrees, the effect of varying the NA of illumination and collection fibers was assessed as a function of center-to-center distance by alternating the illumination and collection fiber NAs between 0.22 and 0.37. The refractive index of the medium above the tissue model was set to 1.45 to simulate an optical fiber and that of the medium below the tissue model was set to 1.0.

The following outputs were calculated from the Monte Carlo simulations: axial fluorescence emission profile, sensitivity to the epithelial layer fluorescence, and total fluorescence detected. The axial fluorescence emission profile is the fluorescence detected by the collection fiber versus the axial depth from which the fluorescent photon originates. The sensitivity to the epithelial layer fluorescence is defined as the ratio of the detected fluorescence originating from the epithelial layer (thickness of 450 μm) and the total detected fluorescence. The total fluorescence detected was calculated by taking the ratio of the number of fluorescent photons detected by the collection fiber to the number of fluorescent photons actually generated within the epithelial tissue model.

Figure 6A:
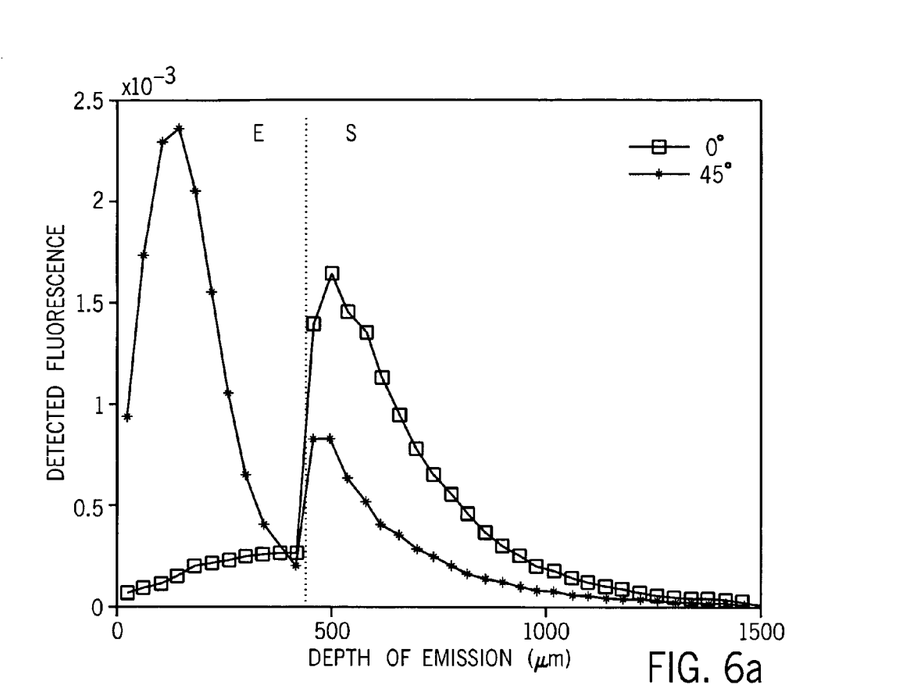
FIG. 6A is a graphic representation of detected fluorescence as a function of tissue depth at a number of different illumination angles.

FIG. 6A shows the detected fluorescence as a function of tissue depth achieved with an illumination tilt angle of 0° and 45° relative to the axis perpendicular to the tissue surface. The dashed line at a depth of 450 μm separates the epithelium (E) and stroma (S) in the theoretical tissue model. At normal incidence (0°), the collection fiber is most sensitive to the fluorescence originating from the stroma side of the epithelial/stromal interface. At an angle of illumination of 45°, the collection fiber is most sensitive to fluorescence originating from the upper-half of the epithelium. It should be noted that the angled illumination probe is most sensitive to fluorescence originating from a sub-surface tissue depth.

Figure 6B:
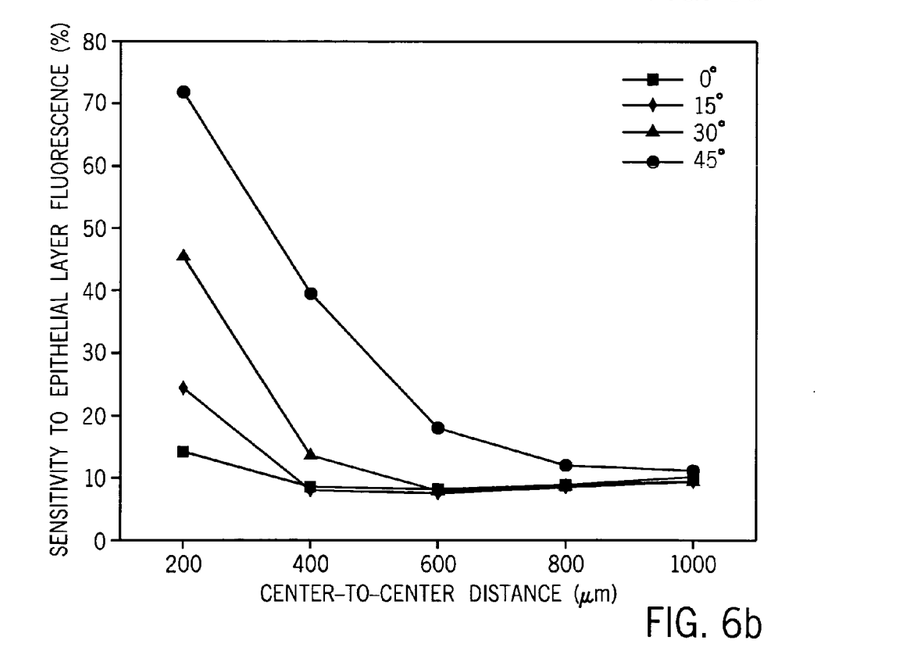
FIG. 6B is a graphic representation of epithelial layer fluorescence as a function of illumination-collection optical fiber separation at a number of different illumination angles.

FIG. 6B shows the sensitivity to the epithelial layer fluorescence as a function of illumination-collection fiber separation or center-to-center distance, at an angle of illumination of 0° (normal incidence), 15°, 30°, and 45°. In the case of normal incidence (0°), the sensitivity to the epithelial layer fluorescence is less than 20% at all separations, suggesting that this probe geometry is more sensitive to stromal layer fluorescence. However, at an angle of illumination of 45°, the sensitivity to the epithelial layer fluorescence is substantially increased at the shortest separation, and increasing the separation provides a wide range of sensitivities to the epithelial and stromal layer fluorescence. Note that varying the angle of illumination has negligible effect on the sensitivity to the epithelial layer fluorescence at illumination-collection separations, exceeding 800 μm. It is also interesting to see that at the shortest illumination-collection separation of 200 μm, a wide range of sensitivities to the epithelial and stromal layer fluorescence can be achieved by varying the illumination fiber tilt angle from 0° to 45°. Varying the NA of the illumination and collection fibers does not affect the sensitivity to the epithelial layer fluorescence.

Figure 6C:
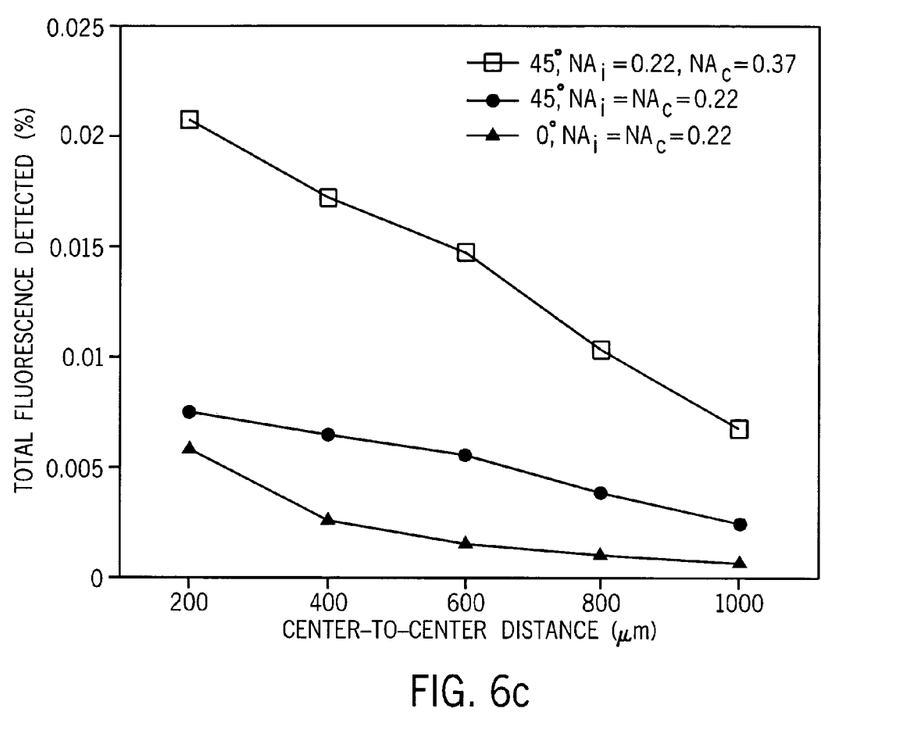
FIG. 6C is a graphic representation of total fluorescence as a function of illumination-collection optical fiber separation at two different illumination angles.

FIG. 6C shows the total fluorescence detected as a function of illumination-collection fiber separation or center-to-center distance, at an illumination angle of 0° (for illumination and collection fiber NAs of 0.22) and at an illumination angle of 45° (for illumination/collection fiber NA pairs of 0.22/0.22 and 0.22/0.37). The total fluorescence detected is greater at all separations for an illumination angle of 45° compared to an illumination angle of 0°. At an angle of illumination of 45°, the total fluorescence detected does not improve if the NA of the illumination fiber is increased, but does improve significantly if the NA of the collection fiber is increased from 0.22 to 0.37.

The angled illumination probe design enables tissue fluorescence to be selectively detected from a wide range of tissue depths and thus has the potential to improve the fluorescence-based diagnosis of epithelial pre-cancers with the conventionally used unshielded and shielded probe geometries. The use of oblique incidence rather than normal incidence on the tissue surface causes the excitation photons and the subsequently generated emission photons to travel a shorter path length before they reach the collection fiber. Thus, increasing the incidence angle of illumination increases the sensitivity to the superficial tissue layer fluorescence. By varying the illumination tilt angle from normal incidence to 45° for example, the depth from which the maximum detected fluorescence originates can be varied between the stromal and epithelial layers and within the different sub-layers of the epithelium. In the angled illumination probe design, the total fluorescence detected increases with (1) increasing illumination incidence angle relative to the normal, (2) decreasing illumination-detection center-to-center distance and (3) increasing collection fiber NA. All three of these factors increase the overlap between illumination and collection light cones in the tissue thus increasing the total fluorescence detected.

Simulations indicate that similar results are achieved if the detection fiber is positioned at different incidence angles θ and the illumination fiber is fixed normal to the tissue surface. Thus, control over the depth at which fluorescence is detected may be achieved by changing any of the spacing between the illumination and detection optical fibers, the incidence angle of illumination, or the incidence angle of detection. Finer control can be achieved by combining any two or all three of these mechanisms.

DESCRIPTION OF THE PREFERRED EMBODIMENT

Figure 7:
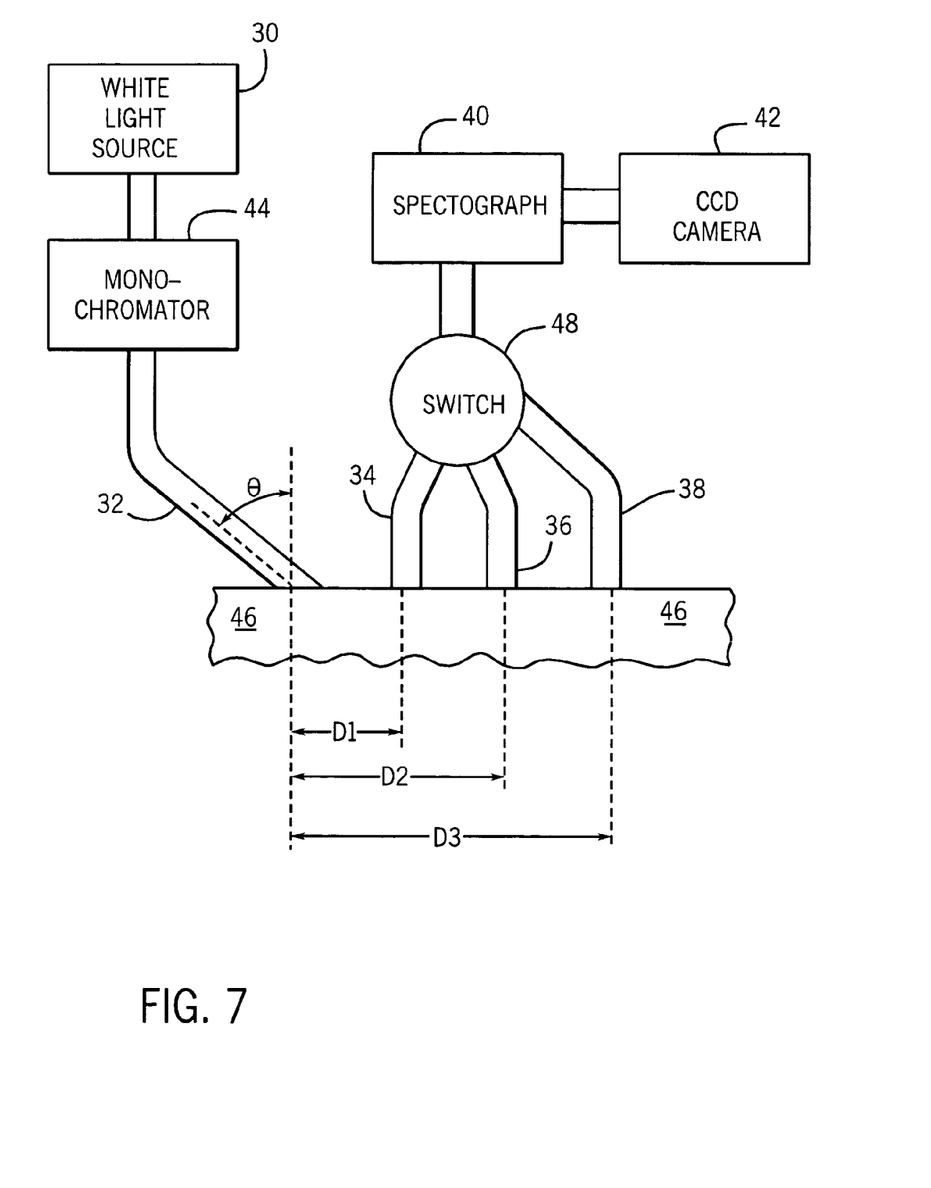
FIG. 7 is a pictorial representation of a fluorescence instrument which employs a preferred embodiment of the present invention.

FIG. 7 shows one preferred embodiment of a fluorescence instrument, which employs the present invention. The primary components are: a filtered white light source 30, an illuminating optical fiber bundle 32, collection optical fiber bundles 34, 36 and 38 and a spectrograph 40 and a detector in the form of a charged couple device (CCD) camera 42. Light emanating from the white light source 30 contains a full spectrum, and a monochromator 44 allows only the light at a selected wavelength to pass through to the illumination bundle 32. The illumination bundle 32 consists of multiple optical fibers, each with the same diameter (200 μm). The illumination light is delivered to the surface of tissue 46 at an incidence angle θ from perpendicular. In the preferred embodiment this angle θ may be set from 0° to 45°.

The collection bundles 34, 36 and 38 are disposed in a line and are placed at different distances from the illumination bundle 32. In the preferred embodiment the collection bundles are spaced at 200 μm center-to-center distances. The collection bundles 34, 36 and 38 are aligned in the direction of the tilted illuminating bundle 32 such that the tissue beneath them is illuminated. The light collected by the collection fibers 34, 36 and 38 is sent to an optical switch 48 which selects the light from one bundle at a time. Measurements of the fluorescence at each of the three collection distances $D_1$, $D_2$ and $D_3$ can thus be made in succession by operating the switch 48 and capturing the light. The light collected by the series of collection fibers 34, 36 and 38 is equivalent to light collected at variable aperture sizes. The incident angle θ is also changed to collect light from different depths beneath the tissue surface.

Figure 8:
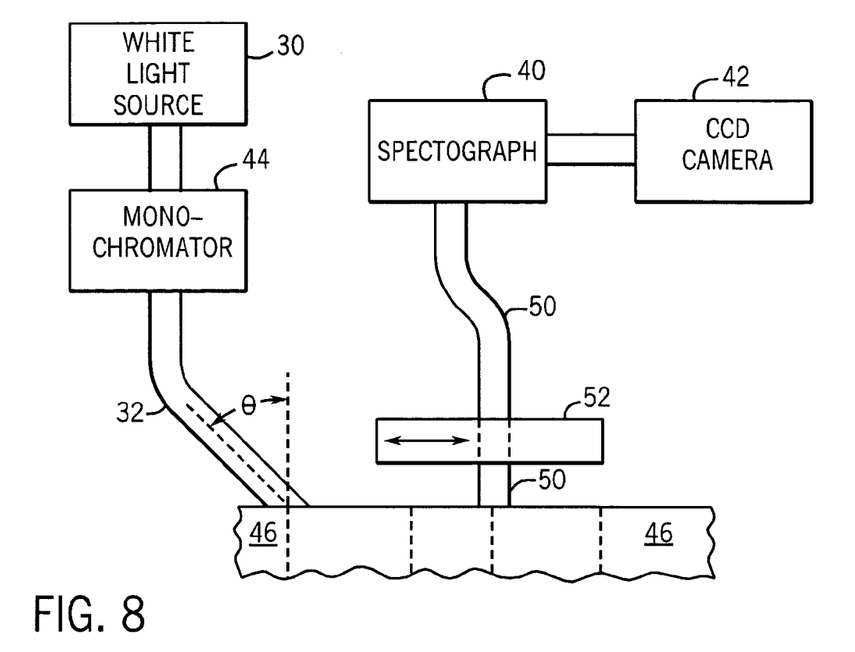
FIG. 8 is a pictorial representation of a fluorescence instrument which employs a second preferred embodiment of the present invention.

Another embodiment of a fluorescence instrument is shown in FIG. 8. This instrument is similar to that described above and shown in FIG. 7 except a single optical fiber collection bundle 50 is employed. No optical switch is therefore needed, but the single collection bundle 50 is moved to different locations on the surface of tissue 46 by a motorized, high resolution translation stage indicated at 52. With this instrument a series of measurements are made with the collection bundle 50 positioned at a corresponding series of locations extending along a path directed away from the illumination bundle 32. These measurements are thus made at a series of different apertures. The incident angle θ is also changed to collect light from different depths beneath the tissue surface.

Figure 10:
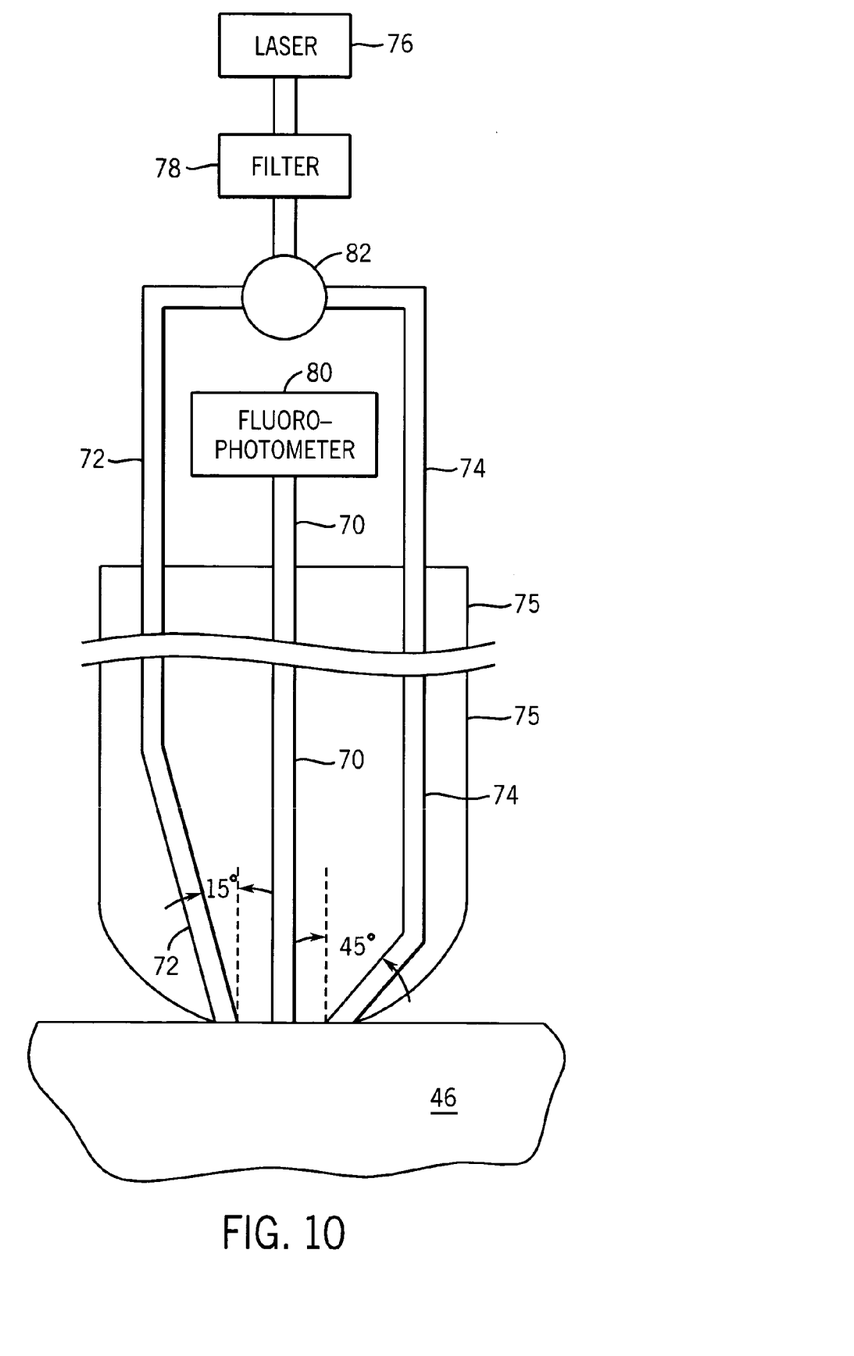
FIG. 10 is a pictorial representation of a fluorescence instrument which employs a third preferred embodiment of the present invention.

In a third embodiment of the fluorescence instrument depicted in FIG. 10, a plurality of illuminating fibers and a single collection fiber are employed. A central collection fiber 70 is fixed perpendicularly to the tissue surface 46, and a pair of illumination fibers 72–74 are disposed on opposite sides of the collection fiber 70. The illumination fibers 72 and 74 are fixed at incidence angles of 15° and 45° respectively with respect to an axis perpendicular to the tissue surface and they are spaced 450 μm from the collection fiber 70. All the fibers have a core diameter of 200 μm and a numerical aperture (NA) of 0.22.

The illumination fibers 72 and 74 are coupled to an argon-ion laser 76 which provides a maximum power of 0.19 W at 351 nm. This output power is attenuated to 1.90 mW by an adjustable aperture and a neutral-density filter 78 before being coupled to the illumination fibers 72 and 74 through a switch 82. The actual output power as measured is 650 μW for the 15° illumination fiber 72 and 300 μW for the 45° illumination fiber 74.

Whereas in the first two embodiments the means for changing the angle of incidence (θ) of the illumination fiber is a mechanism for moving the illumination fiber to the prescribed angle, in the third embodiment the means for changing the angle (θ) is a switch 82. The switch 82 controls which illumination fiber 72 and 74 is energized and hence whether the illumination angle θ is 15° or 45°.

The collection fiber 70 is coupled to the detection module in a fluorophotometer 80. The fluorophotometer 70 includes a double emission scanning monochromator and a photomultiplier tube.

Figure 11:
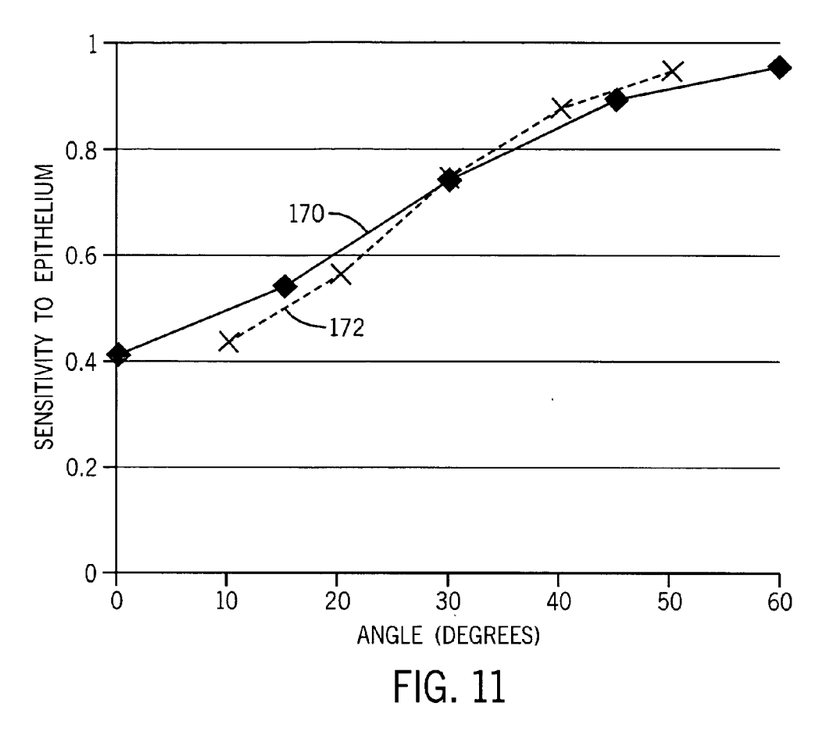
FIG. 11 is a graph showing the relationship of sensitivity to illumination angle and detection angle.

The above embodiments can be modified such that the detector optical fiber is oriented at different collection angles (θ). This can be done in place of different illumination incidence angles or in addition thereto. As shown in FIG. 11, the change in depth sensitivity as a function of changes in illumination incidence angle is indicated by solid line 170. The corresponding relationship of detection angle to depth sensitivity is indicated by dashed line 172 and it can be seen that the relationships are substantially the same.

Figure 12:
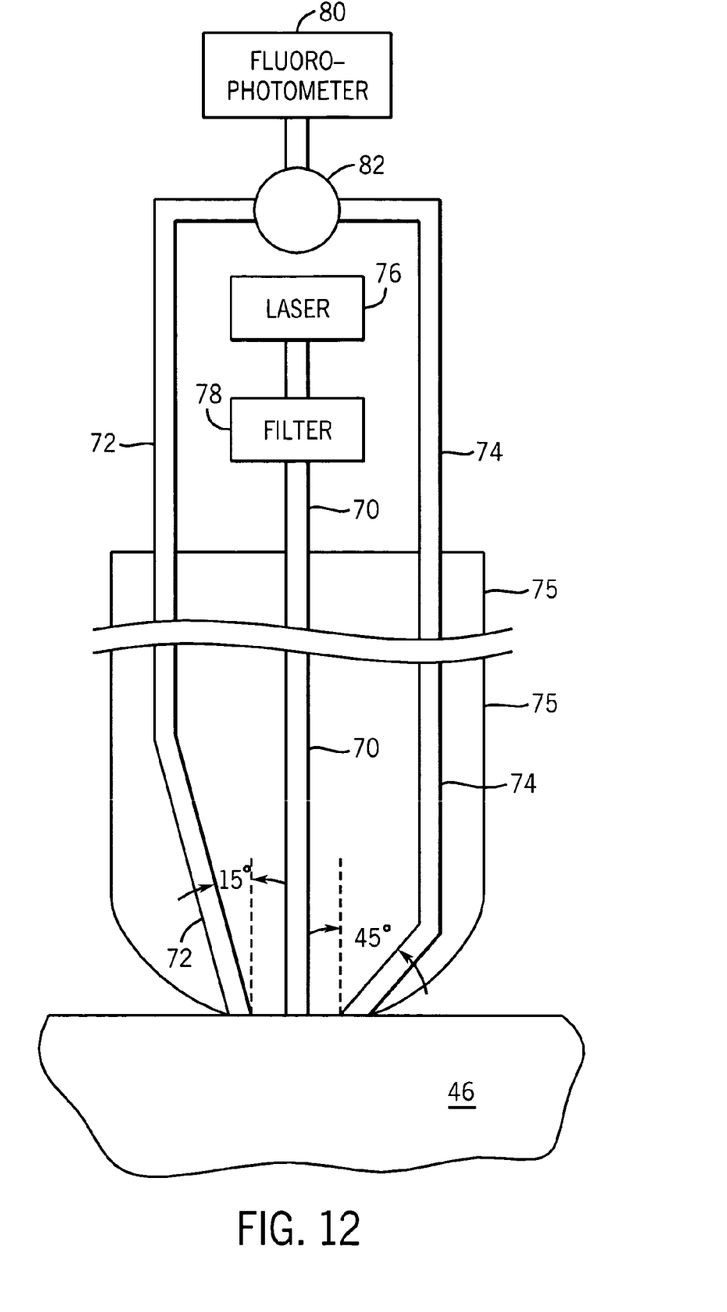
FIG. 12 is a pictorial representation of a fluorescence instrument which employs a fourth preferred embodiment of the invention.

Any of the above-described instruments can be changed to enable detection at different angles. The illumination device and the detection device need only be switched. Referring to FIG. 12, for example, the optical switch 82 can be connected to the input of the fluorophotometer 80 and the optical fiber 70 connected to the output of filter 78. This results in a single illumination fiber 70 and a pair of detector fibers 72 and 74 that enable the detection angle (θ) to be switched to either 15° or 45°.

While all three of the above described fluorescence instruments can be used to acquire fluorescence data at varying depths below a tissue surface, it should be apparent that the embodiment of FIG. 10 is particularly applicable to endoscopic applications because there are no moving parts. In an endoscopic application the two illumination fibers 72 and 74 and the collection fiber 70 are part of an endoscope 75 and they extend from the instrumentation to the distal end of the endoscope 75. They are molded into the fixed, relative positions shown in FIG. 10 at the distal end of the endoscope 75. In use, this distal end is guided to the tissue of interest and pressed against the tissue surface.

Figure 9:
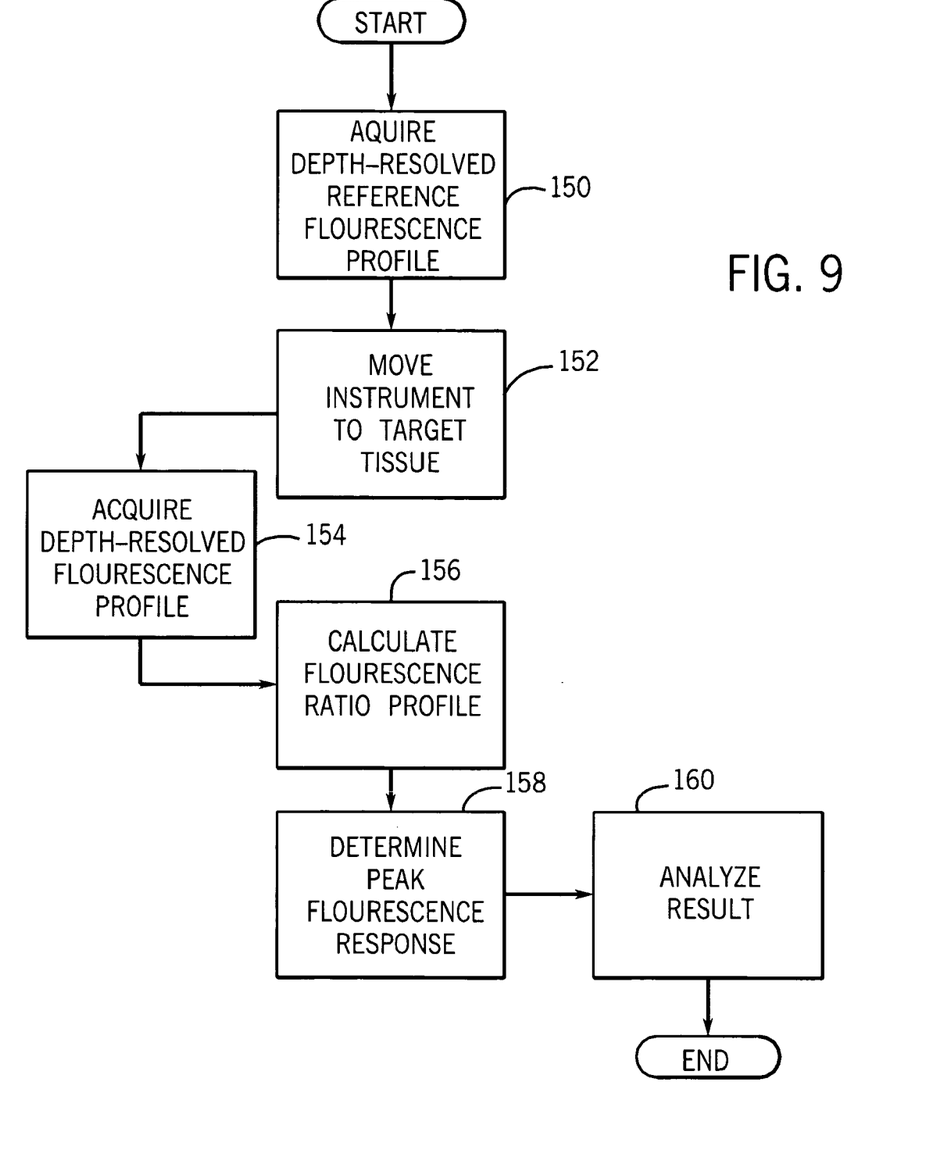
FIG. 9 is a flow chart indicating the steps used to practice the preferred method of using the fluorescence instrument.

Referring particularly to FIG. 9, regardless of which embodiment of the fluorescence instrument is used, a series of measurements are required to acquire sufficient data to assess fluorescence beneath a tissue surface. The first step as indicated at process block 150 is to position the instrument over the surface of "normal" tissue and acquire depth-resolved data. Light at a specific excitation wavelength is selected based on the particular fluorophores being examined and the normal tissue is illuminated at one aperture size and tissue depth. The fluorescence response is collected at this aperture and depth and then stored. Similar measurements are made at each of the prescribed aperture sizes and tissue depths and all the measured fluorescence responses are stored as a reference fluorescence profile. Preferably, these measurements are made a number of times and the results at each setting averaged to provide a more robust reference profile.

As indicated at process block 152, the instrument is then moved to the surface of tissue which is the target of the examination. This may be done, for example, by manipulating an endoscope which carries the optical bundles of the instrument to the desired location. A fluorescence profile of the target tissue is then obtained as indicated at process block 154. This is a repeat of the fluorescence measurements made for the reference profile described above, but the data, of course, may be substantially different depending on the status of the target tissue. The acquired data is stored as a fluorescence profile.

As indicated at process block 156, the next step is to calculate a fluorescence ratio profile. This is performed by calculating the ratio of each aperture fluorescence measurement made at the target tissue and the corresponding aperture fluorescence reference measurement. A smooth curve is fit to the resulting ratio values at each aperture to form the fluorescence ratio profile. This profile of "normalized" fluorescence values is then examined at process block 158 to locate its peak value. The profile peak will be the minimum value in the profile when no exogenous fluorophore (GFP) is employed in the procedure and it will be the maximum value in the profile when an exogenous fluorophore is used. The aperture value and incident angle (θ) at this peak is an indicator of the depth of the fluorescent layer beneath the tissue surface.

The use of oblique incidence rather than normal incidence on the tissue surface causes the excitation photons and the subsequently generated emission photons to travel a shorter path length before they reach the collection fiber. Thus, increasing the angle of illumination increases the sensitivity to the superficial tissue layer fluorescence. By varying the illumination tilt angle from normal incidence to 45° for example, the depth from which the maximum detected fluorescence originates can be varied between the stromal and epithelial layers and within the different sub-layers of the epithelium. The oblique illumination probe provides a superior range of sensitivities to the epithelial and stromal layers than that achieved using prior approaches. Although it has been previously shown that the tissue optical properties and the illumination and collection fiber diameters can affect the sensitivity to the fluorescence originating from different tissue depths, the angled illumination probe design is consistently superior for different sets of optical properties and different fiber diameters.

The invention claimed is:

1. A fluorescence instrument which comprises:
a light source for producing light;
illumination means for conveying the light to the surface of a subject to be examined such that the light may be applied to the surface of the subject at a plurality of incidence angles;
collection means for collecting light emanating from the surface of the subject which is produced by fluorescence within the subject and beneath the surface;
a detector for measuring the collected light; and
means for changing the incidence angle to enable a series of fluorescence measurements of the subject to be made at different depths beneath the surface.

2. The fluorescence instrument as recited in claim 1 in which the illumination means includes a first illumination optical fiber having an end disposed against a first location on said surface; the means for changing alters the angle at which the first illumination optical fiber directs light at the surface; and the collection means includes a collection optical fiber having an end disposed to receive light from a second location on said surface.

3. The fluorescence instrument as recited in claim 2 in which the collection means includes a plurality of said collection optical fibers, each having an end disposed to receive light from a corresponding different second locations on said surface.

4. The fluorescence instrument as recited in claim 1 in which the illumination means includes a first optical fiber oriented such that the light is directed at the surface of the subject at a first incidence angle from a direction perpendicular to the surface, and a second optical fiber oriented such that light is directed at the surface of the subject at a second incidence angle from a direction perpendicular to the surface.

5. The fluorescence instrument as recited in claim 4 in which the subject is tissue, the first incidence angle is substantially 15 and the second incidence angle is substantially 45.

6. The fluorescence instrument as recited in claim 4 in which the means for changing the incidence angle includes a switch for selectively coupling light from the light source to either the first or second optical fiber.

7. The fluorescence instrument as recited in claim 6 in which the collection means includes an optical fiber having an end disposed against the surface.

8. The fluorescence instrument as recited in claim 7 in which the end of the collection optical fiber is disposed between respective ends of the first and second illumination optical fibers.

9. A fluorescence instrument which comprises:
a light source for producing light;
illumination means for conveying the light to the surface of a subject to be examined;
collection means for collecting light emanating from the surface of the subject which is produced by fluorescence within the subject and beneath the surface, such that light may be collected from the surface of the subject at a plurality of collection angles;
a detector for measuring the collected light; and
means for changing the collection angle to enable a series of fluorescence measurements of the subject to be made at different depths beneath the surface.

10. The fluorescence instrument as recited in claim 9 in which the collection means includes a first optical fiber having an end disposed against a first location on said surface; the means for changing alters the angle at which the first optical fiber receives light at the surface; and the illumination means includes an illumination optical fiber having an end disposed to direct light at a second location on said surface.

11. The fluorescence instrument as recited in claim 10 in which the illumination means includes a plurality of said illumination optical fibers, each having an end disposed to direct light at a corresponding different second locations on said surface.

12. The fluorescence instrument as recited in claim 9 in which the collection means includes a first optical fiber oriented such that the light is received from the surface of the subject at a first collection angle, and a second optical fiber oriented such that light is received from the surface of the subject at a second collection angle.

13. The fluorescence instrument as recited in claim 12 in which the subject is tissue, the first collection angle is substantially 15 and the second collection angle is substantially 45 as measured from a direction perpendicular to the surface.

14. The fluorescence instrument as recited in claim 12 in which the means for changing the collection angle includes a switch for selectively coupling light from either the first or second optical fiber to the detector.

15. The fluorescence instrument as recited in claim 14 in which the illumination means includes an illumination optical fiber having an end disposed against the surface.

16. The fluorescence instrument as recited in claim 15 in which the end of the illumination optical fiber is disposed between respective ends of the first and second optical fibers.

17. A method for measuring fluorescence at different depths beneath the surface of an object, the steps comprising:
   a) directing light at the surface of the object at an incidence angle;
   b) collecting light emanating from the surface of the subject at a collection angle, which light is produced by fluorescence within the subject beneath the surface;
   c) detecting the collected light
   d) changing one of the incidence angle and the collection angle; and
   e) repeating steps a), b) and, c) to measure fluorescence within the subject at a plurality of depths beneath the surface.

* * * * *